US 011422285B2

(12) United States Patent
Wang et al.

(10) Patent No.: US 11,422,285 B2
(45) Date of Patent: Aug. 23, 2022

(54) NANOFLUIDIC CHIPS AS MICROMODELS FOR CARBONATE RESERVOIRS

(71) Applicant: Saudi Arabian Oil Company, Dhahran (SA)

(72) Inventors: Wei Wang, Quincy, MA (US); Sehoon Chang, Brighton, MA (US)

(73) Assignee: Saudi Arabian Oil Company, Dhahran (SA)

( * ) Notice: Subject to any disclaimer, the term of this patent is extended or adjusted under 35 U.S.C. 154(b) by 106 days.

(21) Appl. No.: 16/903,903

(22) Filed: Jun. 17, 2020

(65) Prior Publication Data

US 2021/0396907 A1 Dec. 23, 2021

(51) Int. Cl.
| | |
|---|---|
| *G01V 99/00* | (2009.01) |
| *B01L 3/00* | (2006.01) |
| *C01B 33/12* | (2006.01) |
| *E21B 43/16* | (2006.01) |

(52) U.S. Cl.
CPC ...... *G01V 99/005* (2013.01); *B01L 3/502707* (2013.01); *C01B 33/12* (2013.01); *E21B 43/16* (2013.01); *B01L 2300/0896* (2013.01); *B01L 2300/12* (2013.01); *B01L 2300/16* (2013.01); *C01P 2004/32* (2013.01); *C01P 2004/61* (2013.01); *C01P 2004/62* (2013.01); *C01P 2004/64* (2013.01); *E21B 2200/20* (2020.05)

(58) Field of Classification Search
None
See application file for complete search history.

(56) References Cited

U.S. PATENT DOCUMENTS

| | | | |
|---|---|---|---|
| 4,772,563 | A | 9/1988 | Evangelista et al. |
| 4,882,763 | A | 11/1989 | Buchan et al. |
| 5,124,268 | A | 6/1992 | Dakubu |
| 5,168,927 | A | 12/1992 | Stegenneier |
| 6,488,872 | B1 | 12/2002 | Beebe et al. |
| 6,590,647 | B2 | 7/2003 | Stephenson |
| 6,691,780 | B2 | 2/2004 | Nguyen et al. |
| 7,032,662 | B2 | 4/2006 | Malone |
| 7,588,827 | B2 | 9/2009 | Nie et al. |
| 7,875,654 | B2 | 1/2011 | Hong et al. |

(Continued)

FOREIGN PATENT DOCUMENTS

| | | |
|---|---|---|
| EP | 0171978 | 11/1990 |
| EP | 2040075 | 3/2009 |

(Continued)

OTHER PUBLICATIONS

Gogoi er al., "Review on microfluidic studies for EOR application," Journal of Petroleum Exploration and Production Technology, Sep. 2019, 9(3): 2263-2277, 15 pages.

(Continued)

*Primary Examiner* — Jeffrey D Washville
(74) *Attorney, Agent, or Firm* — Fish & Richardson P.C.

(57) ABSTRACT

Methods and systems for generating a nanofluidic chip as a reservoir model are provided. In an example described herein, a nanofluidic chip for reservoir modeling includes a microfluidic chip that includes microchannels etched in a substrate. Silica spheres are assembled in the microchannels to form nanochannels. A carbonate coating is disposed over the surfaces of the nano channels and the silica spheres.

16 Claims, 7 Drawing Sheets

(56) References Cited

U.S. PATENT DOCUMENTS

| | | | |
|---|---|---|---|
| 7,879,625 | B1 | 2/2011 | Boss |
| 8,337,783 | B2 | 12/2012 | Locascio et al. |
| 8,722,812 | B2 | 5/2014 | Yabu et al. |
| 9,708,525 | B2 | 7/2017 | Suresh et al. |
| 9,873,827 | B2 | 1/2018 | Chakraborty et al. |
| 10,316,873 | B2 | 6/2019 | Weitz et al. |
| 10,392,555 | B2 | 8/2019 | Giro et al. |
| 2008/0110253 | A1 | 5/2008 | Stephenson et al. |
| 2008/0111064 | A1 | 5/2008 | Andrews et al. |
| 2008/0206317 | A1 | 8/2008 | Johnsson et al. |
| 2009/0087912 | A1 | 4/2009 | Ramos et al. |
| 2009/0248309 | A1 | 10/2009 | Nelville et al. |
| 2010/0049625 | A1 | 2/2010 | Biebesheimer et al. |
| 2010/0092865 | A1 | 4/2010 | Kanno et al. |
| 2010/0224823 | A1 | 9/2010 | Yin et al. |
| 2010/0305219 | A1 | 12/2010 | Granick et al. |
| 2010/0307745 | A1 | 12/2010 | Lafitte |
| 2011/0012331 | A1 | 1/2011 | Kim |
| 2011/0207231 | A1 | 8/2011 | Natan et al. |
| 2011/0239754 | A1 | 10/2011 | Dyer |
| 2011/0260051 | A1 | 10/2011 | Preudhomme et al. |
| 2011/0275061 | A1 | 11/2011 | Weidemaier et al. |
| 2012/0062886 | A1 | 3/2012 | Piotti |
| 2012/0115128 | A1 | 5/2012 | Miller |
| 2012/0193578 | A1 | 8/2012 | Pan et al. |
| 2012/0257199 | A1 | 10/2012 | Liu et al. |
| 2012/0261617 | A1 | 10/2012 | Pan et al. |
| 2013/0040292 | A1 | 2/2013 | Lopez et al. |
| 2013/0084643 | A1 | 4/2013 | Commarieu et al. |
| 2013/0087329 | A1 | 4/2013 | Hewitt |
| 2013/0259808 | A1 | 10/2013 | Chen et al. |
| 2014/0077121 | A1 | 3/2014 | Sun et al. |
| 2014/0186939 | A1 | 7/2014 | Peterman et al. |
| 2014/0231077 | A1 | 8/2014 | Rivero et al. |
| 2014/0260694 | A1 | 9/2014 | Szlendak |
| 2014/0323363 | A1 | 10/2014 | Perriat |
| 2014/0360973 | A1 | 12/2014 | Yin et al. |
| 2015/0038347 | A1 | 2/2015 | Johnson et al. |
| 2015/0079270 | A1 | 3/2015 | Wang et al. |
| 2015/0175876 | A1 | 6/2015 | Resasco et al. |
| 2015/0299369 | A1 | 10/2015 | Ausserre et al. |
| 2016/0003040 | A1 | 1/2016 | Jessheim et al. |
| 2016/0097750 | A1 | 4/2016 | Van Herzen |
| 2016/0271513 | A1* | 9/2016 | Weitz .................. C01F 11/181 |
| 2017/0173546 | A1 | 6/2017 | Cheng et al. |
| 2017/0199124 | A1 | 7/2017 | Bolduc et al. |
| 2018/0275114 | A1 | 9/2018 | Kosynkin |
| 2019/0016943 | A1 | 1/2019 | Ren et al. |

FOREIGN PATENT DOCUMENTS

| | | |
|---|---|---|
| EP | 2104082 | 9/2009 |
| EP | 2480625 | 4/2013 |
| EP | 2480626 | 4/2013 |
| WO | WO 2010138914 | 12/2010 |
| WO | WO 2011035294 | 3/2011 |
| WO | WO 2011035292 | 10/2011 |
| WO | WO 2014014919 | 1/2014 |
| WO | WO 2015058206 | 4/2015 |
| WO | WO 2015097116 | 7/2015 |
| WO | WO 2015200060 | 12/2015 |
| WO | WO 2016087397 | 6/2016 |
| WO | WO 2017015120 | 1/2017 |
| WO | WO 2017136641 | 8/2017 |
| WO | WO 2017164822 | 9/2017 |
| WO | WO 2017210424 | 12/2017 |
| WO | WO 2019027817 | 2/2019 |

OTHER PUBLICATIONS

Wang et al.,"Toward Reservoir-on-a-Chip: Fabricating Reservoir Micromodels by in Situ Growing Calcium Carbonate Nanocrystals in Microfluidic Channel," Applied Materials & Interfaces, Aug. 2017, 9(34): 29380-29386, 21 pages.

Wang et al., "Self-assembly of two and three-dimensional particle arrays by manipulating the hydrophobicity of silica nanospheres," Journal of Physical Chemistry, Nov. 2005, 109(47): 22175-22180, 6 pages.

Yu et al., "New insights into flow physics in the EOR process based on 2.5D reservoir micromodels," Journal of Petroleum Science and Engineering, Jun. 2019, 181, XP085751272, 13 pages.

Zhang et al., "Geomaterial-Functionalized Microfluidic Devices Using a Universal Surface Modification Approach," Advanced Materials Interfaces, Oct. 2019, 6(23): 1900995, 16 pages.

PCT International Search Report and Written Opinion in International Appln. No. PCT/US2021/036394, dated Sep. 10, 2021, 15 pages.

Agenet et al., "Fluorescent Nanobeads: a First Step Toward Intelligent Water Tracers," SPE-157019, Society of Petroleum Engineers (SPE), presented at the SPE International Oilfield Nanotechnology Conference held in Noordwijk, the Netherlands, Jun. 12-14, 2012, 13 pages.

Anisimov, "The Use of Tracers for Reservoir Characterization," SPE-118862, Society of Petroleum Engineers (SPE), presented at SPE Middle East Oil and Gas Show and Conference, Mar. 15-18, 2009, 8 pages.

Armelao et al., "Design of luminescent lanthanide complexes: From molecules to highly efficient photo-emitting materials," Coordination Chemistry Reviews 254: 5-6, Mar. 2010, 19 pages.

Aslan et al., "Fluorescent Core—Shell AG@$SiO_2$ Nanocomposites for Metal-Enhanced Fluorescence and Single Nanoparticle Sensing Platforms," JACS Communications, J. Am. Chem. Soc. 129: 1524-1525, Jan. 19, 2007, 2 pages.

Badgett et al., "Totalsynthese eines Neobetanidin-Derivates und des Neobetenamins," Helvetica Chimica Acta 53(2): 433-448, 1970, 16 pages, English Summary.

Bao et al., "Luminescence properties of the co-luminescence groups of Sm-La-pyridyl carboxylic acids," Journal of Rare Earths 30:4 (320-324), Apr. 2012, 5 pages.

Borrini et al., "Water Soluble PDCA Derivatives for Selective Ln(III)/An(III) and Am(III)/Cm(III) Separation," Solvent Extraction and Ion Exchange 33:3 (224-235), Oct. 2014, 30 pages.

Brichart et al., "The Use of Fluorescent Tracers for Inhibitor Concentration Monitoring Useful for Scale Inhibitor," IPTC-17933-MS, International Petroleum Technology Conference, presented at the International Petroleum Technology Conference held in Kuala Lumpur, Dec. 10-12, 2014, 8 pages.

Bunzil et al., "Taking advantage of luminescent lanthanide ions," The Royal Society of Chemistry, Chemical Society Reviews 34: 1048-1077, Dec. 2005, 30 pages.

Chang et al., "Magnetic SERS Composite Nanoparticles for Microfluidic Detection," 251st ACS National Meeting, Mar. 13-17, 2016, 1 pages, abstract only.

Chen et al., "Analysis of the solution conformations of T4 lysozyme by paramagnetic NMR spectroscopy," The Royal Society of Chemistry, Physical Chemistry Chemical Physics (PCCP) 18:8 (5850-5859), 2016, 10 pages.

Chen et al., "Impact of Irreversible Retention on Tracer Deployments; Constraining Novel Material Deployments," SPE 188890-MS, Society of Petroleum Engineers (SPE), presented at the SPE Abu Dhabi International Petroleum Exhibition and Conference, Nov. 2017, 8 pages.

Chen et al., "Improved Reservoir History Matching and Production Optimization with Tracer Data," SPE 191523-MS, Society of Petroleum Engineers (SPE), presented at the SPE Annual Technical Conference and Exhibition, Sep. 2018, 15 pages.

Chen et al., "FITC functionalized magnetic core-shell $Fe_3O_4$/Ag hybrid nanoparticle for selective determination of molecular biothiols," Sensorts and Actuators B: Chemical 193: 857-863, 2014, 7 pages.

Chuang et al., "Ultra-sensitive in-situ detection of novel near-infrared persistent luminescent tracer nanoagents in crude oil-water mixtures," a natureresearch journal, Scientific Reports, Jun. 15, 2016, 5 pages.

Coates et al, "Enhancement of luminescence of europium(m) ions in water by use of synergistic chelation. Part 1.1:1 and 2:1 com-

(56) References Cited

OTHER PUBLICATIONS plexes," J. Chem. Soc, Perkin Trans. 2 (1275-1282), Jan. 1996, 8 pages.
Constantin and Davidson, "Lamellar La mesophases doped with inorganicnanoparticles," Minireview, Chem. Phys. Chem. 15: 1270-1282, 2014, 12 pages.
Cubillos et al., "The Value of Inter-well and Single Well Tracer Technology for De-Risking and Optimizing a CEOR Process—Caracara Field Case," SPE 174394-MS, Society of Petroleum Engineers (SPE), presented at the EUROPEC 2015, Jun. 1-4, 2015, 19 pages.
Das et al., "Molecular Fluorescence, Phosphorescence, and Chemiluminescence Spectrometry," American Chemical Society (ACS Publications), Analytical Chemistry 84: S7-625, Nov. 3, 2011, 29 pages.
Deans, "Using Chemical Tracers to Measure Fractional Flow and Saturation In-Situ," SPE-7076, Society of Petroleum Engineers (SPE), presented at SPE Symposium on improved Methods of Oil Recovery, Apr. 16-17, 1978, 10 pages.
Du and Guan, "Interwell tracer tests: lessons learned from past field studies," SPE 93140-MS, Society of Petroleum Engineers (SPE), presented at the SPE Asia Pacific Oil and Gas Conference and Exhibition, Apr. 5-7, 2005, 9 pages.
Dugstad, "Chapter 6: Well-to-well tracer tests," in Petroleum Engineering Handbook, 5: 651-683, 2007, 31 pages.
Edwards et al., "Extending the distance range accessed with continuous wave EPR with Gd3+ spin probes at high magnetic fields," The Royal Society of Chemistry, Physical Chemistry Chemical Physics (PCCP) 15:27 (11313-11326), 2013, 14 pages.
El-Aneed et al., "Mass Spectrometry, Review of the Basics: Electrospray, MALDI, and Commonly Used Mass Analyzers," Applied Spectroscopy Reviews 44:3 (210-230), Mar. 16, 2009, 22 pages.
Esmaeilzadeh et al., "Effect of ZrO2 nanoparticles on the interfacial behavior of surfactant solutions at airwater and n-heptane-water interfaces," Fluid Phase Equilibria 361: 289-295, 2014, 7 pages.
Freeze and Cherry, "Chapter 9: Groundwater Contamination," in Groundwater, Englewood Cliffs, NJ: Prentice-Hall, Inc., 1979, 80 pages.
Galdiga and Greibrokk, "Ultra-trace determination of flurinated aromatic carboxylic acids in aqueous reservoir fluids using solid-phase extraction in combination with gas chromatography-mass spectrometry," Journal of Chromatography A 793:2 (297-306), Jan. 16, 1998, 10 pages.
Gao et al., "A Surface Functional Monomer-Directing Strategy for Highly Dense Imprinting of TNT at Surface of Silica Nanoparticles," JACS Communications, Journal of American Chemical Society 129:25 (7859-7866), Jun. 2007, 8 pages.
Gardiner et al., "Practical Raman Spectroscopy," Springer-Verlag, 1989, 9 pages.
George et al., "Modified Dipicolinic Acid Ligands for Sensitation and Europium (III) Luminescence," Inorganic Chemistry 45:4 (1739-1744), Feb. 1, 2006, 6 pages.
Gordon-Grossman et al., "W-Band pulse EPR distance measurements in peptides using Gd3+-dipicolinic acid derivatives as spin labels," Physical Chemistry Chemical Physics 13:22 (10771-10780), 2011, 10 pages.
Grutzke et al., "Heptacoordinate Heteroleptic Salan (ONNO) and Thiosalan (OSSO) Titanium(IV) Complexes: Investigation of Stability and Cytotoxicity," American Chemical Society (ACS Publications), Inorganic Chemistry 54:14 (6697-6706), Jul. 2015, 10 pages.
Hagoot, "The response of interwell tracer tests in watered-out reservoirs," SPE 11131-MS, Society of Petroleum Engineers (SPE), presented at the 57th Annual Fall Technical Conference and Exhibition of the Society of Petroleum Engineers of AIME, Sep. 1982, 21 pages.
Han et al., "Application of Silver-Coated Magnetic Microspheres to a SERS-Based Optofluidic Sensor," American Chemical Society (ACS Publications), The Journal of Physical Chemistry (JPCC) 115: 6290-6296, Mar. 7, 2011, 7 pages.

He et al., "Luminescent Europium Chelates Synthesis and Fluorescence Properties," Sensors and Materials 19:2 (123-132), 2007, 10 pages.
He et al., "One-pot Facile Synthesis of Janus Particles with Tailored Shape and Functionality," Electronic Supplementary Material (ESI) for Chemical Communications, The Royal Society of Chemistry, 2011, 17 pages.
Holm et al., "Synthesis, Characterization, and Light-Induced Spatial Charge Separation in Janus Graphene Oxide," American Chemical Society (ACS Publications), Chemistry of Materials (CM) 30: 2084-2092, 2018, 9 pages.
hoteng.com (online), "Microfluidic Solutions for IOR/EOR Optimisation: Rapid and Cost Efficient EOR Screening using a Rock-on-a-Chip Approach," HOT Engineering GmbH, retrieved from URL <https://www.hoteng.com/microfluidic-solutions/#1457967643112-9de392c4-0c28>, retrieved on Jun. 2, 2020, available on or before Mar. 2019, 8 pages.
Hu et al, "Fabrication, properties and applications of Janus particles," The Royal Society of Chemistry, Chem. Soc. Rev. 41:11 (4356-4378), Feb. 2012, 23 pages.
Hu et al., "Smart Liquid SERS Substrates based on Fe3O4/Au Nanoparticles with Reversibly Tunable Enhancement Factor for Practical Quantitative Detection," Scientific Report 4: 7204 (1-10), Nov. 2014, 10 pages.
Huseby et al., "Assessing EOR potential from partitioning tracer data," SPE 172808-MS, Society of Petroleum Engineers (SPE), presented at the SPE Middle East Oil and Gas Show and Conference, Mar. 2015, 15 pages.
Huseby et al., "High Quality Flow Information from Tracer Data," SPE-169183-MS, Society of Petroleum Engineers (SPE), presented at the SPE Bergen One Day Seminar, Apr. 2, 2014, 9 pages.
Hutchins et al., "Aqueous Tracers for Oilfield Applications," SPE-21049, Society of Petroleum Engineers (SPE), presented at SPE International Symposium on Oilfield Chemistry, Feb. 20-22, 1991, 9 pages.
Jenkins et al., "Ultratrace Determination of Selected Lanthanides by Luminescence Enhancement," Analytical Chemistry 68:17 (2974-2980), Sep. 1, 1996, 7 pages.
Jun et al., "Multifunctional Silver-Embedded Magnetic Nanoparticles as SERS Nanoprobes and Their Applications," Wiley-VCH Verlag GmbH& Co. KGaA, Weinheim, Small 6:1 (119-125), Jan. 4, 2010, 7 pages.
Kaushik et al., "Gd(III) and Mn(II) complexes for dynamic nuclear polarization: small molecular chelate polarizing agents and applications with site-directed spin labeling of proteins," The Royal Society of Chemistry, Physical Chemistry Chemical Physics (PCCP) 18:39 (27205-27218), 2016, 36 pages.
Khan et al., "Optimizing waterflood management in a giant UAE carbonate oil field using simulation-based streamlines," SPE 171777-MS, Society of Petroleum Engineers (SPE), presented at the Abu Dhabi International Petroleum Exhibition and Conference, Nov. 10-13, 2014, 9 pages.
Kneipp et al., "Single Molecule Detection Using Surface-Enhanced Raman Scattering (SERS)," Physical Review Letters, American Physical Society 78:9, Mar. 3, 1997, 4 pages.
Kornberger and Thiele, "Experiences with an Efficient Rate-Management Approach for the 8th Tortonian Reservoir in the Vienna Basin," SPE 166393-PA, Society of Petroleum Engineers (SPE), presented at the SPE Annual Technical Conference and Exhibition, Sep. 30-Oct. 2, 2013, SPE Reservoir Evaluation and Engineering 17:2, May 2014, 12 pages.
Kosynkin and Alaskar, "Oil Industry First Interwell Trial of Reservoir Nanoagent Tracers," SPE 181551-MS, Society of Petroleum Engineers (SPE), presented at the SPE Annual Technical Conference and Exhibition, Sep. 2016, 15 pages.
Labbe et al., "Development of metal-chelating inhibitors for the Class II fructose 1,6-bisphosphate (FBP) aldolase," Journal of Inorganic Biochemistry 112: 49-58, Jul. 2012, 10 pages.
Larsen et al, "Efficient Synthesis of 4,7-Diamino Substituted 1,10-Phenanthroline-2,9-dicarboxamides," American Chemical Society (ACS Publications), Organic Letters 13:13 (3546-3548), Jul. 1, 2011.

(56) References Cited

OTHER PUBLICATIONS

Li et al., "Magic Angle Spinning NMR Structure Determination of Proteins from Pseudocontact Shifts," JACS Communications, Journal of the American Chemical Society 135:22 (8294-8303), May 2013, 10 pages.
Li et al., "Thiol-ene reaction: a versatile tool in site-specific labelling of proteins with chemically inert tags for paramagnetic NMR," The Royal Society of Chemistry, Chemical Communications, Cambridge, United Kingdom 48:21 (2704-2706), 2012, 18 pages.
Luo et al., "Nanofluid of graphene-based amphiphilic Janus nanosheets for tertiary or enhanced oil recovery: High performance at low concentration," PNAS 113: 7711-7716, 2016, 6 pages.
Luo et al., "Secondary Oil Recovery Using Graphene-Based Amphiphilic JanusNanosheet Fluid at an Ultralow Concentration," American Chemical Society (ACS Publications), Industrial & Engineering Chemistry Research (I&EC Research), 56: 11125-11132, Sep. 2017, 25 pages.
Manna et al, "Complexation behavior of trivalent actinides and lanthanides with 1,10-phenanthroline-2,9-dicarboxylic acid based ligands: insight from density functional theory," Physical Chemistry Chemical Physics (PCCP) 14:31 (11060), Jan. 1, 2012, 10 pages.
Marais et al., "Time-Resolved Fluorescence for Real-Time Monitoring of Both Scale and Corrosion Inhibitors: a Game-Changing Technique," SPE 179867, Society of Petroleum Engineers (SPE), presented at the SPE International Oilfield Scale Conference and Exhibition held in Aberdeen, Scotland, May 11-12, 2016 11 pages.
Marchetti et al., "Fluorous affinity chromatography for enrichment and determination of perfluoroalkyl substances," American Chemical Society (ACS Publications), Annual Review of Analytical Chemistiy 84: 7138-7145, Jul. 19, 2012, 8 pages.
Martini et al., "How to Monitor Scale Inhibitor Squeeze using Simple TRF Tracers," SPE-173768-MS, Society of Petroleum Engineers (SPE), presented at the SPE International Symposium on Oilfield Chemistry held in the Woodlands, Texas, Apr. 13-15, 2015, 8 pages.
McGrail et al., "Selective mono-facial modification of grapheneoxide nanosheets in suspension," The Royal Society of Chemistry, Chem. Commun, 52: 288-291, 2016, 5 pages.
Melton et al, "Complexes of Greatly Enhanced Thermodynamic Stability and Metal Ion Size-Based Selectivity, Formed by the Highly Preorganized Non-Macrocyclic Ligand 1,10-Phenanthroline-2,9-dicarboxylic Acid: A Thermodynamic and Crystallographic Study," Inorganic Chemistry 45:23 (9306-9314), Nov. 1, 2006, 9 pages.
micronit.com (online), "Enhanced oil recovery," retrieved from URL <https://www.micronit.com/products/enhanced-oil-recovery.html>, retrieved on Mar. 10, 2020, 5 pages.
micronit.com, "Lab-on-a-chip and MEMS Solutions," retrieved from URL <https://www.micronit.com/>, retrieved on Jun. 2, 2020, available on or before Mar. 19, 2018 via wayback machine URL <https://web.archive.org/web/20180319182410/https://www.micronit.com/>, 7 pages.
Moyner et al., "The Application of Flow Diagnostics for Reservoir Management," Society of Petroleum Engineers (SPE), SPE Journal, Apr. 2015, 18 pages.
Muller and Seubert, "Ultra trace determination of fluorobenzoic acids in tap and reservoir water using solid-phase extraction and gas chromatography-mass spectrometry," Journal of Chromatography A, 1260: Oct. 9-15, 2012, 7 pages.
Negin et al., "Application of nanotechnology for enhancing oil recovery—A review," Ke Ai Advanced Research Evolving Science, Petroleum 2: 324-333, 2016, 10 pages.
Negin et al., "Most common surfactants employed in chemical enhanced oil recovery," Petroleum 3: 197-211, 2017, 32 pages.
Ng et al., "Graphene-based two-dimensional Janus materials," NPG Asia Materials 10:4 (217-237), Apr. 2018, 21 pages.
Nie et al., "Probing Single Molecules and Single Nanoparticles by Surface-Enhanced Raman Scattering," Science 275:5303 (1102-1106), Feb. 21, 1997, 6 pages.
Ogden et al., "Complexation of Am(III) and Nd(in) by 1,10-Phenanthroli ne-2,9-Di carboxylic Acid," Journal of Solution Chemistry 42:1 (211-225), 2013, 15 pages.
Ouali et al., "Analysis of Paramagnetic NMR Spectra of Triple-Helical Lanthanide Complexes with 2,6-Dipicolinic Acid Revisited: A New Assignment of Structural Changes and Crystal-Field Effects 25 Years Later," Inorganic Chemistry 41:6 (1436-1445), Feb. 2002, 10 pages.
Pallenberg et al. "Synthesis and Characterization of Some Copper(I) Phenanthroline Complexes" Inorg. Chem. 34: 2833-2840, 1995, 8 pages.
Parker and Williams, "Getting excited about lanthanide complexation chemistry," Journal of the Chemical Society, Dalton Transactions 18, 1996, 16 pages.
Parker et al., "Being excited by lanthanide coordination complexes: aqua species, chirality, excited-state chemistry, and exchange dynamics," Chemical Reviews 102:6, May 2002, 34 pages.
Peng et al., "A review of nanomaterials for nanofluid enhanced oil and recovery," The Royal Society of Chemistry, RSC Advances 7: 32246-32254, Jun. 13, 2017, 9 pages.
Petoud et al., "Brilliant SM, Eu, Tb, and Dy Chiral Lanthanide Complexes with Strong Circularly Polarized Luminescence," JACS Communications, Journal of the American Chemical Society 2017:129 (77-83), Dec. 15, 2006, 7 pages.
Potapov et al., "Nanometer-Scale Distance Measurements in Proteins Using Gd3+ Spin Labeling," Journal of the American Chemical Society, 132:26 (9040-9048), Jun. 2010, 9 pages.
Qianming et al., "Bspda Synthesis and its Europium (III) Complexes' Fluorescence," Chemical Industry Times, Jul. 2005, 19(7): 38-41, 4 pages (English Abstract).
Rashadan et al., "Effect of the preparation route, PEG and annealing on the phase stability of Fe3O4 nanoparticles and their magnetic properties," Journal of Experimental Nanoscience 8:2 (210-222), 2013, 14 pages.
Rowan et al., "Dynamic Covalent Chemistry," Angewante Chemie International Edition 41: 898-952, Mar. 15, 2002, 55 pages.
Sabbatini et al., "Luminescent lanthanide complexes as photochemical supramolecular devices," Coordination Chemistry Reviews 123: Feb. 1-2, 1993, 28 pages.
Sammes and Yshioglu, "Modem bioassays using metal chelates as luminescent probes," Natural Product Reports, 31:1, 1996, 28 pages.
Sanni et al., "A field case study of inter-well chemical tracer test," SPE-173760-MS, Society of Petroleum Engineers (SPE), in SPE International Symposium on Oilfield Chemistry, Apr. 2015, 17 pages.
Sanni et al., "Pushing the envelope of residual oil measurement: A field case study of a new class of inter-well chemical tracers," Journal of Petroleum Science and Engineering 163, 2018, 19 pages.
Schmidt et al., "Copper dipicolinates as peptidomimetic ligands for the Src SH2 domain," Bioorganic & Medicinal Chemistry Letters, 14:16 (4203-4206), Aug. 2004, 4 pages.
Schmidt et al., "Synthesis of Mono- and Dinuclear Vanadium Complexes and Their Reactivity toward Dehydroperoxidation of Alkyl Hydroperoxides," Inorganic Chemistry 56:3 (1319-1332), 2017, 14 pages.
Selvin et al., "Principles and biophysical applications of lanthanide-based probes," Annual Review of Biophysics and Biomolecular Structure 31: 275-302, Jun. 2002, 28 pages.
Serres-Piole et al., "Direct sensitive simultaneous determination of fluorinated benzoic acids in oil reservoir waters by ultra high-performance liquid chromatography-tandem mass spectrometry," Journal of Chromatography A, 1218, Aug. 2011, 6 pages.
Serres-Piole et al., "Water tracers in oilfield applications: Guidelines," Elsevier Ltd., Journal of Science and Engineering 98-99: 22-39, Nov. 2012, 18 pages.
Sharma and Mohanty, "Wettability Alteration in High-temperature and High-salinity Carbonate Reservoirs," SPE 147306, Society of Petroleum Engineers (SPE), presented at the SPE Annual Technical Conference and Exhibition, Oct. 30-Nov. 2, 2011, SPE Journal 18:4 (646-655), Aug. 2013, 10 pages.
Shook et al., "Determining Reservoir Properties and Flood Performance from Tracer Test Analysis," SPE 124614, Society of Petro-

(56) References Cited

OTHER PUBLICATIONS leum Engineers (SPE), presented at SPE Annual Technical Conference and Exhibition, Oct. 4-7, 2009, 19 pages.
Solomon et al., "Synthesis and Study of Silver Nanoparticles," Journal of Chemical Education 84:2 (332-325), 2007, 4 pages.
Song et al., "SERS-Encoded Nanogapped Plasmonic Nanoparticles: Growth of Metallic Nanoshell by Templating Redox-Active Polymer Brushes," JACS Communications, Journal of the American Chemical Society 136: 6838-6841, Apr. 28, 2014, 4 pages.
Stiles et al., "Surface-Enhanced Raman Spectroscopy," Annual Review of Analytical Chemistry 1: 601-626, Mar. 18, 2008, 29 pages.
Stryer et al., "Diffusion-enhanced fluorescence energy transfer," Annual Review of Biophysics and bioengineering 11:1, 1982, 21 pages.
Su et al., "A Dipicolinic Acid Tag for Rigid Lanthanide Tagging of Proteins and Paramagnetic NMR Spectroscopy," Journal of the American Chemical Society, 130:32 (10486-10487), Jul. 2008, 2 pages.
Tang et al., "Synthesis and fluorescence properties of Tb(III) complexes with pyridine-2,6-dicarboxylic acid derivatives," Journal of Central South University of Technology (English Edition) 15:5 (599-605), Oct. 2008, 7 pages.
Tang et al., "Synthesis of Novel Derivatives of Pyridine-2,6-dicarboxylic Acid," Synthetic Communications: An International Journal for Rapid Communication of Synthetic Organic Chemistiy 36:14 (2027-2034), Jun. 2006, 9 pages.
Tang et al., "Synthesis of Eu(III) and Tb(III) Complexes with Novel Pyridine-2,6-Dicarboxylic Acid Derivatives and Their Fluorescence Properties," Front. Chem. China 4: 408-413, 2006, 6 pages.
Tian et al., "Off-Resonant Gold Superstructures as Ultrabright Minimally Invasive Surface-Enhanced Raman Scattering (SERS) Probes," American Chemical Society (ACS Publications), Chemistry of Materials (CM) 27: 5678-5684, Jul. 2015, 7 pages.
Toulhoat, "Experimentation and Modelling of U, Th and Lanthanides Transport in Fissured Rocks: Influence of Complexation," MRS Proceedings 50, Jan. 1, 1985, 8 pages.
Vatanparast et al., "Wettability alteration of low-permeable carbonate reservoir rocks in presence of mixed ionic surfactants," Petroleum Science and Technology 29:18 (1873-1884), 2011, 14 pages.
Walther et al., "Janus Particles: Synthesis, Self-Assembly, Physical Properties and Applications," American Chemical Society (ACS Publications), Chem. Rev. 113:7 (5194-5261), Apr. 2013, 68 pages.
Wang et al., "The Design and Implementation of a Full Field Inter-Well Tracer Program on a Giant UAE Carbonate Oil Field," SPE-177527-MS, Society of Petroleum Engineers (SPE), in Abu Dhabi International Petroleum Exhibition and Conference, Nov. 2015, 8 pages.
Wu et al., "A reusable biosensor chip for SERS-fluorescence dual mode immunoassay," Proc. SPIE 9543: 954317-1, presented at the Third International Symposium on Laser Interaction with Matter (LIMIS), May 4, 2015, 6 pages.
Wu et al., "A SERS-Assisted 3D Barcode Chip for High-Throughput Biosensing," Material Views Full Papers, Small Journal 11:23 (2798-2806), Jun. 11, 2015, 9 pages.
Xu et al., "Measurement of two-photon excitation cross sections of molecular fluorophores with data from 690 to 1050 nm," Journal of the Optical Society of America B 13:3, Mar. 1996, 11 pages.
Yang et al., "The Co-Luminescence Groups of Sm-La-pyridyl Carboxylic Acids and the Binding Characteristics between the Selected Doped Complex and Bovine Serum Albumin," Bulletin of the Korean Chemical Society 33:4 (1303-1309), Apr. 20, 2012, 7 pages.
Yang et al., "Paramagnetic labeling of proteins and pseudocontact shift in structural biology," Chinese Journal of Magnetic Resonance, 2014, 31:2 (155-171), English Abstract.
Zamberi et al., "Improved Reservoir Surveillance Through Injected Tracers in a Saudi Arabian Field: Case Study," SPE 166005, Society of Petroleum Engineers (SPE), presented at the SPE Reservoir Characterization and Simulation Conference and Exhibition, Sep. 16-18, 2013, 15 pages.
Zemel, "Chapter 3: Tracers in the Oil Field," in Tracers in the Oil Field, Technology and Engineering, Elsevier 43, Jan. 1995, 47 pages.
Zhang et al., "Janus Particles: Synthesis, Self-Assembly, Physical Properties, and Applications," American Chemical Society (ACS Publications), Langmuir 33: 6964-6977, 2017, 14 pages.
Zhang et al., "Novel zwitterionic surfactant derived from castor oil and its performance evaluation for oil recovery," Colloids Surfaces A: Physicochemical and Engineering Aspects 483: 87-95, 2015, 42 pages.
Zhou et al., "Upconversion luminescent materials: advances and applications," American Chemical Society (ACS Publications), Chemical Reviews, 115: 395-465, Jan. 14, 2015, 71 pages.

* cited by examiner

NANOFLUIDIC CHIPS AS MICROMODELS FOR CARBONATE RESERVOIRS

BACKGROUND

With the growth of worldwide demand for oil and the decline of the discovery rate of new oil fields, it is important to improve the oil production efficiency of current fields. Further, many of the world's reservoirs trap about two thirds of the oil in place, which cannot be recovered by conventional production methods. To increase oil recovery efficiency, it is important to better understand multiphase fluid behaviors and interactions among oil-water-rock phases in underground oil reservoirs.

A significant proportion of the world's oil reserves are found in carbonate reservoirs. For example, it is estimated that around 70% of oil and 90% of gas reserves are held in carbonate reservoirs in the Middle East. Generally, carbonate rocks are mainly composed of calcite ($CaCO_3$) and dolomite ($CaMg(CO_3)_2$). Based on studies on carbonate reservoir rocks in Arabian Peninsula, at typical reservoir depths the calcite content is greater than 90 wt. % and even up to 100 wt. % at certain depth.

Reservoir micromodels, such as microfluidic chips, have been widely used to mimic the underground oil-reservoir environment for multi-phase flow studies, enhanced oil recovery, and reservoir network mapping. However, currently available micromodels have porosities at micrometer (or larger) scales which limits the investigation and visualization of fluid properties at submicron scales. Further, most of the micromodels are constructed of glass or polymer materials, limiting their representation of the properties of a geochemical surface of the carbonate reservoir rocks.

SUMMARY

An embodiment disclosed herein provides a method for modeling a reservoir with a nanofluidic chip. The method includes fabricating the nanofluidic chip by synthesizing silicon dioxide spheres and functionalizing a surface of the silicon dioxide spheres to form functionalized spheres. A surface of microchannels in a glass (fused silica) microfluidic chip is functionalized to form a functionalized microfluidic chip. The functionalized spheres are assembled in microchannels of the functionalized microfluidic chip to form a precursor nanofluidic chip. Calcium carbonate nanocrystals are formed on functionalized surfaces of the precursor nanofluidic chip to form the nanofluidic chip.

Another embodiment described herein provides a nanofluidic chip for reservoir modeling includes a microfluidic chip comprising microchannels etched in a substrate. Silica (silicon dioxide, $SiO_2$) spheres assembled in the microchannels form nanochannels. A carbonate coating is disposed over the surfaces of the nanochannels and the silica spheres.

DETAILED DESCRIPTION

Figure 1:
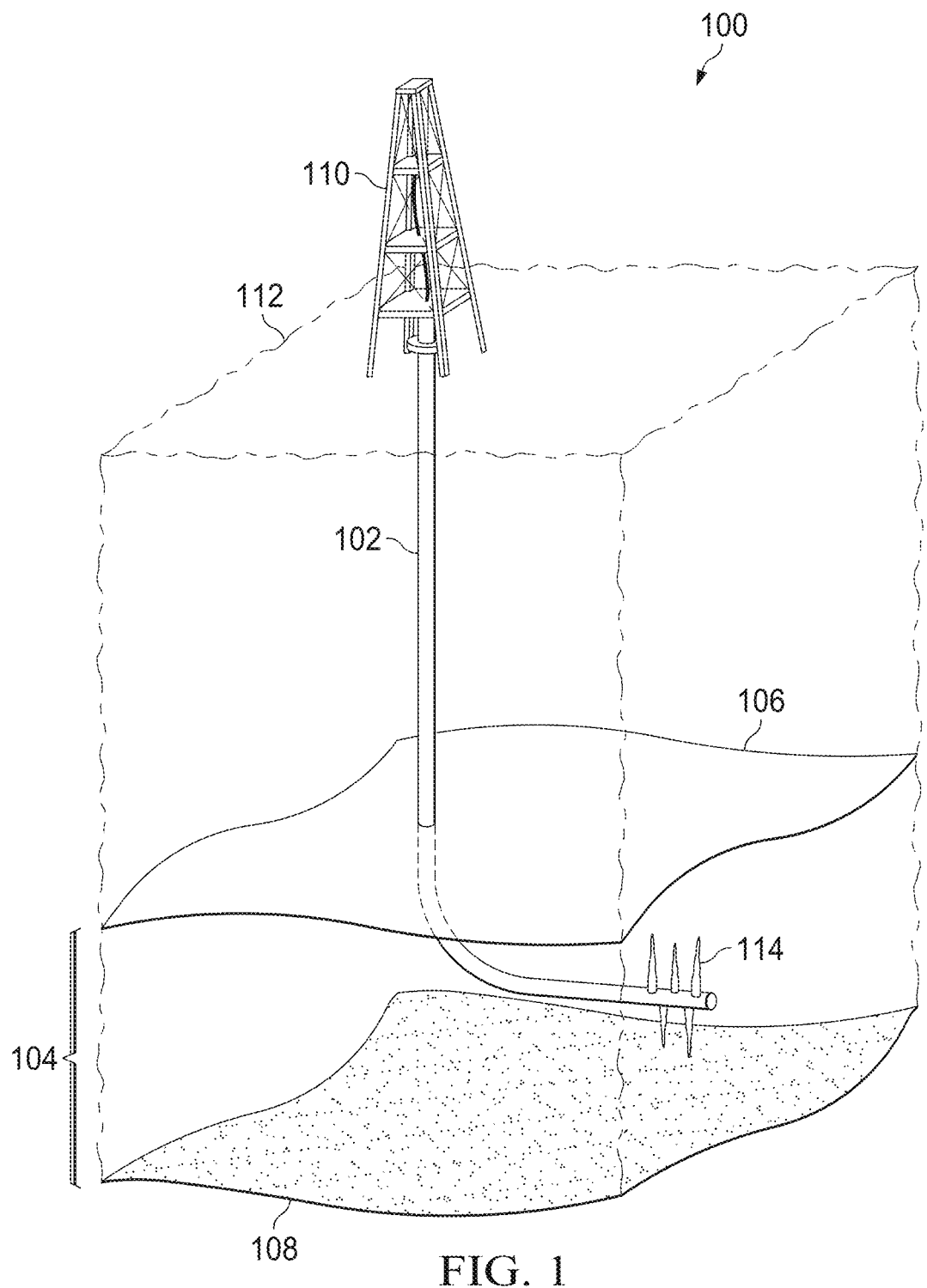
FIG. 1 is a drawing of a wellbore drilled into a carbonate reservoir layer.

In the field of research about oil reservoir and enhanced oil recovery (EOR), it is desirable to have a micromodel with controllable porosity at submicron scale and with surface property of carbonates. Current commercial EOR microfluidic chips have two dimensional (2D) microchannels that are about 20 µm to about 200 µm in size. However, carbonate reservoirs may have smaller channel sizes, e.g., less than about 1 µm. The current techniques for fabricating microchannels in microfluidic chips, often based on photo-etching of a substrate, do not adequately scale to smaller channel sizes, such as channel sizes below 1 µm. Accordingly, there is no commercially available nanofluidic chip with nanoscale channels and porosity, termed channels herein, especially for those made by optical transparent materials such as glass and polymers.

In the techniques described herein are directed to a chemical procedure to fabricate such nanofluidic chips with nanoscale channels, and surface of calcium carbonate, calcium magnesium carbonate, e.g., $CaCO_3$, $CaMg(CO_3)_2$, or both. The nanofluidic chips can be used as carbonate micromodels for oil and gas reservoir applications.

In the fabrication process described herein, silica (silicon dioxide, $SiO_2$) spheres that are substantially monodisperse and in controlled sizes, both in micron and nanometer ranges of 50-2500 nm, are synthesized via a colloidal synthesis method. The surfaces of the silica spheres and of the microfluidic channels in a microfluidic chip are then functionalized. The silica spheres are assembled within the microfluidic channels of a microfluidic chip to form a random close packing (RCP) structure. After assembly, the surfaces, both of the silica spheres and of the microfluidic channels, are coated by in situ growing of a thin layer of $CaCO_3$ nanocrystals, simulating calcite, or a layer of nanocrystals that includes $CaMg(CO_3)_3$, simulating dolomite. Because the nanocrystal coated spheres are densely packed in a near three-dimensional (3D) close-packed colloidal structure, the network of voids between the silica spheres forms nanoscale channels. Column experiments and computer simulations have shown that the approximately 64% of the volume fraction of space is occupied by the spheres in a random closest packing configuration, i.e. ~36% space is left as voids between the spheres. In a microfluidic chip, similar density of packed spheres is expected and the desired porosity is controlled by the size of silica spheres. For example, larger spheres will provide larger channels. In close-packed sphere geometry, it can form a tetrahedral void since the four spheres surrounding it arranged on the corners of a regular tetrahedron, or an octahedral void since the six spheres surrounding it lie at the corners of a regular octahedron. If R denotes the radius of the $SiO_2$ spheres surrounding a tetrahedral or an octahedral void, the radius of the spheres that would just fit into the voids are given by 0.225R or 0.414R, respectively. Therefore, sizes of nanofluidic channels can be 0.225-0.414 of the $SiO_2$ sphere sizes used to fabricate the nanofluidic channels. With $SiO_2$ spheres in size range of 50-2500 nm, the voids can be created in controllable size range about 10-1000 nm.

The size of the nanospheres varies from tens of nanometer to several thousands of nanometer in diameter to form the 3D dense pack in the tens or hundreds of micrometer size channels of the chips. In some embodiments, the largest nanoscale channels in a nanofluidic chip are less than about 1000 nm. In other embodiments, the channels are less than about 20 nm. For example, 1200 nm $SiO_2$ spheres can generate channels in range of about 254 nm to about 497 nm, and 200 nm $SiO_2$ spheres can generate channels in range of about 42 nm to about 83 nm.

The new carbonate nanofluidic chips provide a simple and useful micromodel system for modeling a reservoir, allowing the study of oil-water phase behavior and the interactions between fluids and surfaces, such as rock-fluid interactions, at nanoscale porosities using small volume of samples and at low cost. The nanofluidic chips are optically transparent, allowing interactions between fluids and the surfaces to be directly visualized by multiple characterization tools, such as advanced spectroscopic and microscopic techniques, providing useful information for enhanced oil recovery.

FIG. 1 is a drawing 100 of a wellbore 102 drilled into a carbonate reservoir layer 104. In this illustration, the carbonate reservoir layer 104 is bounded by an upper layer 106, such as a layer of cap rock, and a lower layer 108, such as a salt layer.

In the drawing 100, a drilling rig 110, or other completion equipment, at the surface 112 is used to treat the wellbore 102 in the carbonate reservoir layer 104. This may be done by techniques that create fractures or other openings 114 in the carbonate reservoir layer 104. For example, acid treatment may be used to create the openings 114.

Understanding the multiphase flow behavior in the carbonate reservoir layer 104 is important to determining the best treatment to maximize production. As described herein, the fabricated nanofluidic chip can be used as a micromodel system to study multiphase fluid behavior. The usefulness of the nanofluidic chip has been demonstrated for a water flooding experiment for studying oil replacement in the nano-pore channels, and for an electrokinetic fluid diffusion experiment with dead-end structured nanopores.

Figure 2:
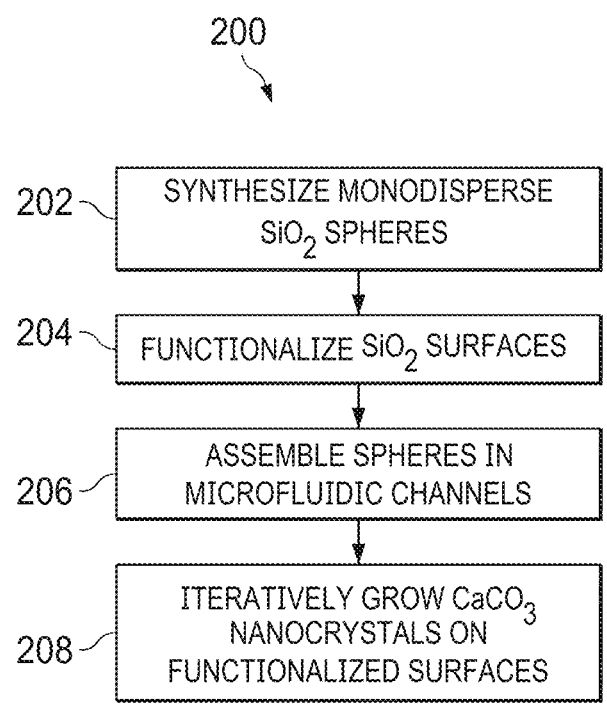
FIG. 2 is a process flow diagram of a method for fabricating a nanofluidic chip as a micromodel for a carbonate reservoir.

FIG. 2 is a process flow diagram of a method 200 for fabricating a nanofluidic chip as a micromodel for a carbonate reservoir. The procedure creates nanoscale porosities, or channels, in calcium carbonate ($CaCO_3$) fluidic chips. The nanofluidic chips are fabricated from commercially available glass or quartz microfluidic chips with two-dimensional (2D) microsized channels and porosity. Various microfluidic chips with micrometer porosity (micropores or microchannels) are commercially available, such as a glass enhanced oil recovery (EOR) chip available from Micronit Company of the Netherlands or glass-silicon-glass EOR/JOR rock-on-a-chip from HOT Engineering GMBH.

Generally, monodisperse $SiO_2$ colloidal nanospheres or microspheres are assembled in the 2D microchannels of the EOR chip to form a 3D random close packed (RCP) structure within the microchannels. This creates voids between the $SiO_2$ spheres, and the network of 3D connected voids form channels. The size of the channels can be controlled in the nanoscale, or submicron, range depending on the sizes of $SiO_2$ spheres used. To enable the channels to chemically resemble a carbonate reservoir, calcium carbonate nanocrystals are formed on the surface of the $SiO_2$ of these spheres and the microchannels through an in-situ chemical coating process. The $CaCO_3$ layer also immobilizes the $SiO_2$ spheres within the microfluidic chips. Thus, fully carbonate surfaced microfluidic chips with channels having a nanoscale, termed nanofluidic chips herein, are fabricated.

The method begins at block 202 with the synthesis of monodisperse $SiO_2$ spheres. The monodisperse spheres can be made with different sizes both in the micrometer and nanometer ranges, depending on the target scale for the channels in the nanofluidic chips. Generally, the synthesis is based on the hydrolysis reaction of tetraalkylorthosilicate compounds in a water-alcohol mixture with ammonia as a catalyst. The synthesis method is discussed further with respect in the examples below. Examples of the monodisperse spheres is shown in the scanning electron micrograph of FIG. 3.

Figure 4:
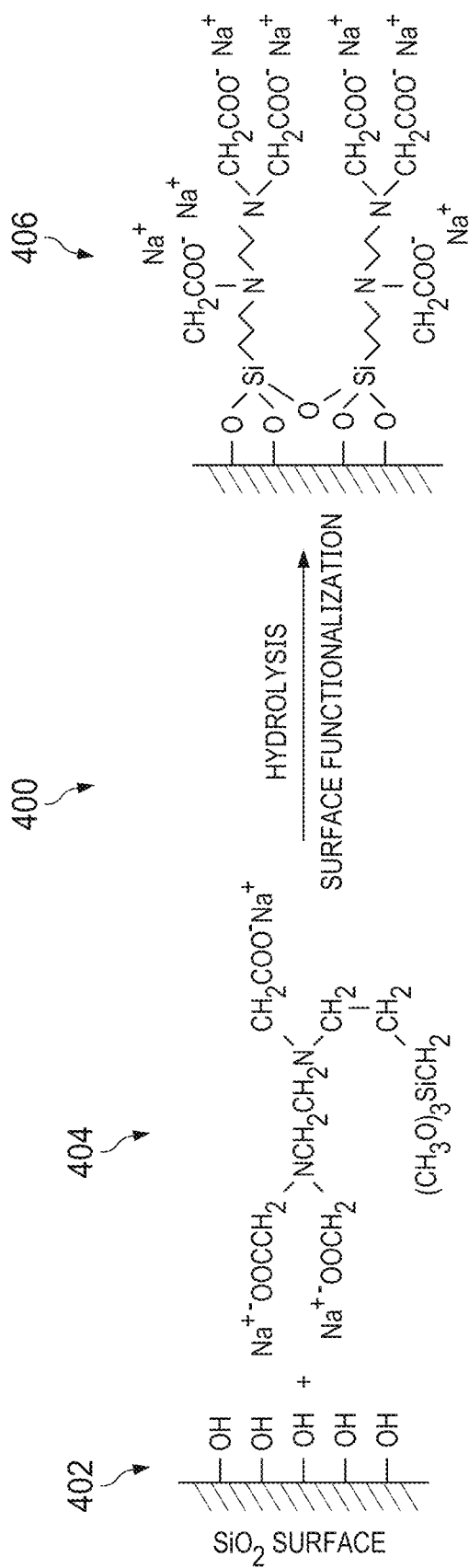
FIG. 4 is a schematic diagram of the functionalization of the $SiO_2$ surfaces of the spheres and the microchannels of the microfluidic chip.

At block 204, the surfaces of the spheres are functionalized by chemically grafting carboxylate groups onto the surface using a silane coupling agent. This is performed by first hydrolyzing the surfaces to form hydroxyl groups, then reacting the hydrolyzed surface with the silane coupling agent. The same treatment is performed on the surface of microchannels in the microfluidic chip to form a functionalized microfluidic chip. The same silane coupling agent, or a different silane coupling agent, may be used for each surface. An example of the hydrolysis and functionalization of the surfaces is shown in FIG. 4, with N-(trimethoxysilylpropyl) ethylene diaminetriacetate as the silane coupling agent. Other silane coupling agents that can be used include trimethoxysilylpropyl modified (polyethylenimine), or 3-(trihydroxysilyl) propyl methylphosphonate, among others. Combinations of silane coupling agents may be used to adjust the properties.

At block 206, the spheres are assembled in the microchannels of the EOR chip. In an embodiment, monodisperse and surface-functionalized spheres are suspended in ethanol to form a colloidal suspension. The colloidal suspension is injected into the EOR chip, and the spheres are caught in the microchannels to form a random close packing (RCP) structure. The measured void volume fraction between the spheres is about 30% to about 42% of the whole spheres occupied space. The voids between the spheres create channels at a nanometer scale depending on the size of the spheres used, allowing control over the size of channels. As used herein, this creates a precursor nanofluidic chip. In some embodiments, two or more different sizes of functionalized spheres (varying from 400 nm to 1200 nm) are used to create different sizes of channels in the precursor nanofluidic chip.

At block 208, calcite crystals are grown on the functionalized surfaces of the spheres and microchannels in the precursor nanofluidic chip, creating the nanofluidic chip. This may be performed by iteratively flowing solutions of calcium chloride ($CaCl_2$)) and sodium carbonate ($Na_2CO_3$) through the precursor nanofluidic chip. As each solution flows through the chip, material is added to the surfaces, forming a calcium carbonate ($CaCO_3$) surface. Generally, five to 10 iterations are used to form a thin layer of $CaCO_3$ on the silica surface through the net reaction:

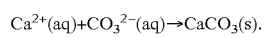

$$Ca^{2+}(aq)+CO_3^{2-}(aq) \rightarrow CaCO_3(s).$$

This surface layer is not limited to calcium carbonate, which simulates calcite, but may also include magnesium carbonate ($MgCO_3$) in combination with the calcium carbonate to simulate a dolomite surface. The composition may be used to adjust the surface properties to more closely match the chemical composition of a particular carbonate reservoir. For example, other elements may also be included in the solutions to form the thin layer, including, for example, aluminum, silicon, zinc, iron, copper, manganese, titanium, vanadium, or other elements, or combinations of elements, which may be found in target reservoirs.

After the formation of the thin calcium carbonate, or calcium/magnesium carbonate layer, the nanofluidic chip may be used for testing of water flooding, carbon dioxide flooding, separations, phase treatments, acid treatments, and other enhanced oil recovery techniques.

EXAMPLES

Materials

The materials used for the synthesis of $SiO_2$ nanoparticle were tetraethyl orthosilicate (TEOS, 99%) and $NH_3.H_2O$ (29.4%), obtained from Fluka and J. T. Baker, respectively. For the functionalization and assembly of the nanospheres in the microfluidic chip, absolute ethanol, chloroform, 2-propanol (99.5%), and NaOH solution (1 N) were obtained from EM Science. The silane coupling agent used for functionalizing the spheres and the microchannels of the microchips was (trimethoxysilylpropyl) ethylenediaminetriacetate trisodium (35% in water) obtained from Gelest.

Formation of Monodisperse $SiO_2$ Spheres

Monodisperse $SiO_2$ spheres were prepared by hydrolyzing TEOS in an alcoholic medium in the presence of water and ammonia using a modified procedure originally known as the Stober reaction. Typical preparation is to rapidly mix two equal-volume parts with a total volume of 250 mL one includes alcohol and TEOS, while another one includes alcohol, water, and ammonia. Fixed concentrations of 17.0 M $H_2O$ and 1.63 M $NH_3$ in ethanol were used for the synthesis of $SiO_2$ nanoparticles, and the resulting particle sizes were controlled by varying TEOS concentration and temperature. Depending on the TEOS concentration and reaction temperature, the reaction mixture appeared to be turbid white in 2-15 min, as $SiO_2$ particles were formed. The sizes of the spheres depended on the concentration of the TEOS, for examples, 400 nm particles from 0.2M TEOS at 25° C., 800 nm $SiO_2$ from 0.3M TEOS at 18° C., and 1200 nm $SiO_2$ from 0.6M TEOS at 10° C., respectively. The reaction was continued for greater than about 6 hrs with moderate stirring at room temperature. $SiO_2$ spheres can be synthesized in size range of 50-2500 nm depending on different reaction parameters.

Figure 3A:
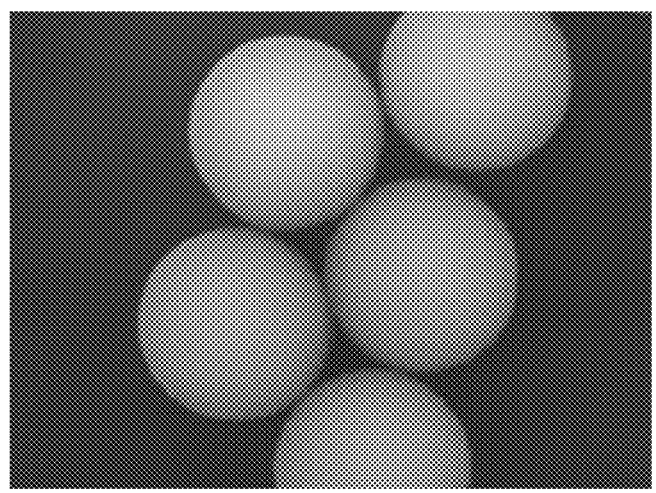
FIGS. 3A-3C are scanning electron micrographs of $SiO_2$ spheres with different sizes in the nanometer and micrometer range.
Figure 3B:
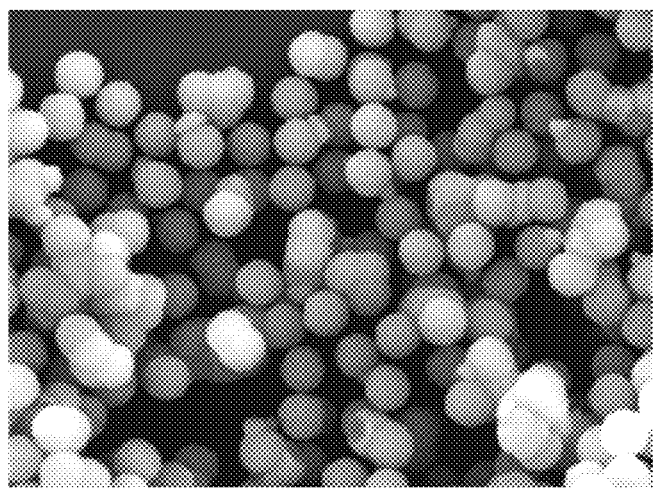
Figure 3C:
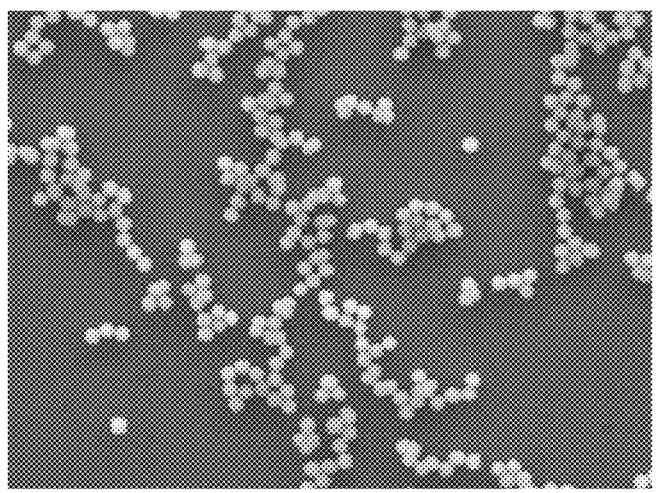

FIGS. 3A-3C are scanning electron micrographs of $SiO_2$ spheres with different sizes in the nanometer and micrometer range. FIG. 3A shows spheres with a diameter of about 650 nm, which provides channels of about 138 nm to about 269 nm in size in a random close packing configuration. FIG. 3B shows spheres with a diameter of about 1 μm, which provides channels of about 212 nm to about 414 nm in size in an RCP configuration. FIG. 3C shows spheres with a diameter of about 400 nm, which provides channels of about 85 nm to about 166 nm in size in an RCP configuration.

The SEM images were taken by scanning electron microscopy (SEM, JEOL, JSM-7100F field emission) at 5 kV, and no additional coating was applied onto the sample surface. The same instrument with EDX analysis (Oxford Instruments) at 20 kV was used for elemental analysis imaging with the results as described with respect to FIG. 7.

Functionalization of $SiO_2$ Surfaces

FIG. 4 is a schematic diagram of the functionalization 400 of the $SiO_2$ surfaces of the spheres and the microchannels of the microfluidic chip. As described herein this is performed prior to injecting the spheres into the microfluidic chip. In some embodiments, spheres may be injected into the microfluidic chip prior to functionalization, and the functionalization may be performed for both the spheres and the channels of the microfluidic chip at the same time.

To begin, the surfaces of glass (fused $SiO_2$) microfluidic chips are hydrolyzed to provide an increased number of —OH groups. This was performed by reacting the surfaces with Piranha solution (typically a mixture of 3 parts of concentrated sulfuric acid and 1 part of 30% hydrogen peroxide solution) or an aqueous base (such as 1M NaOH solution).

The hydrolyzed surface 402 is functionalized by chemically grafting carboxylate groups (—COO$^-$) to the hydrolyzed surface 402 using a silane coupling agent that reacts with the OH groups, for example, the coupling agent 404 (N-(trimethoxysilylpropyl) ethylenediaminetriacetate, sodium salt) shown in FIG. 4.

In this example, the $SiO_2$ spheres and microchannels were surface-functionalized respectively, before assembling the $SiO_2$ spheres into the microchannels of chip. To functionalize the surface of glass microchannel (EOR chip), 2 mL silane coupling agent, N-(trimethoxysilylpropyl) ethylenediaminetriacetate trisodium was first mixed with 10 mL of a chloroform-water solution (volume ratio 1:1) under magnetic stirring. The pH value of the mixture was adjusted to ~1.5 using hydrochloric acid, which solubilized the silane molecules in the chloroform phase. The chloroform phase containing the silane molecules was pumped through the microchannels of the microfluidic chip at 0.1 mL/min for 2-5 min. and allow to sit in the microchannels for 15 min. before removed by an air flow. This process was repeated for 3-5 times then the microchannels were rinsed with ethanol and 0.05 M $CaCl_2$) solution and dried at 60° C. for overnight. To functionalize the $SiO_2$ spheres, upon the synthetic reaction completion in 6 hrs for $SiO_2$ formation, 2 mL silane coupling agent, N-(trimethoxysilylpropyl) ethylenediaminetriacetate trisodium was added to the reaction solution, and the reaction was allowed for additional 12 hrs for completion.

The resulting functionalized surface 406 has accessible carboxylate groups coupled to the surface. Once the carboxylate groups are grafted to the spheres and the internal surfaces of the microfluidic chip, the nanofluidic chip can be assembled by injecting the spheres into the microfluidic chip, as described with respect to FIG. 2.

Assembling the Nanofluidic Chip

Figure 5:
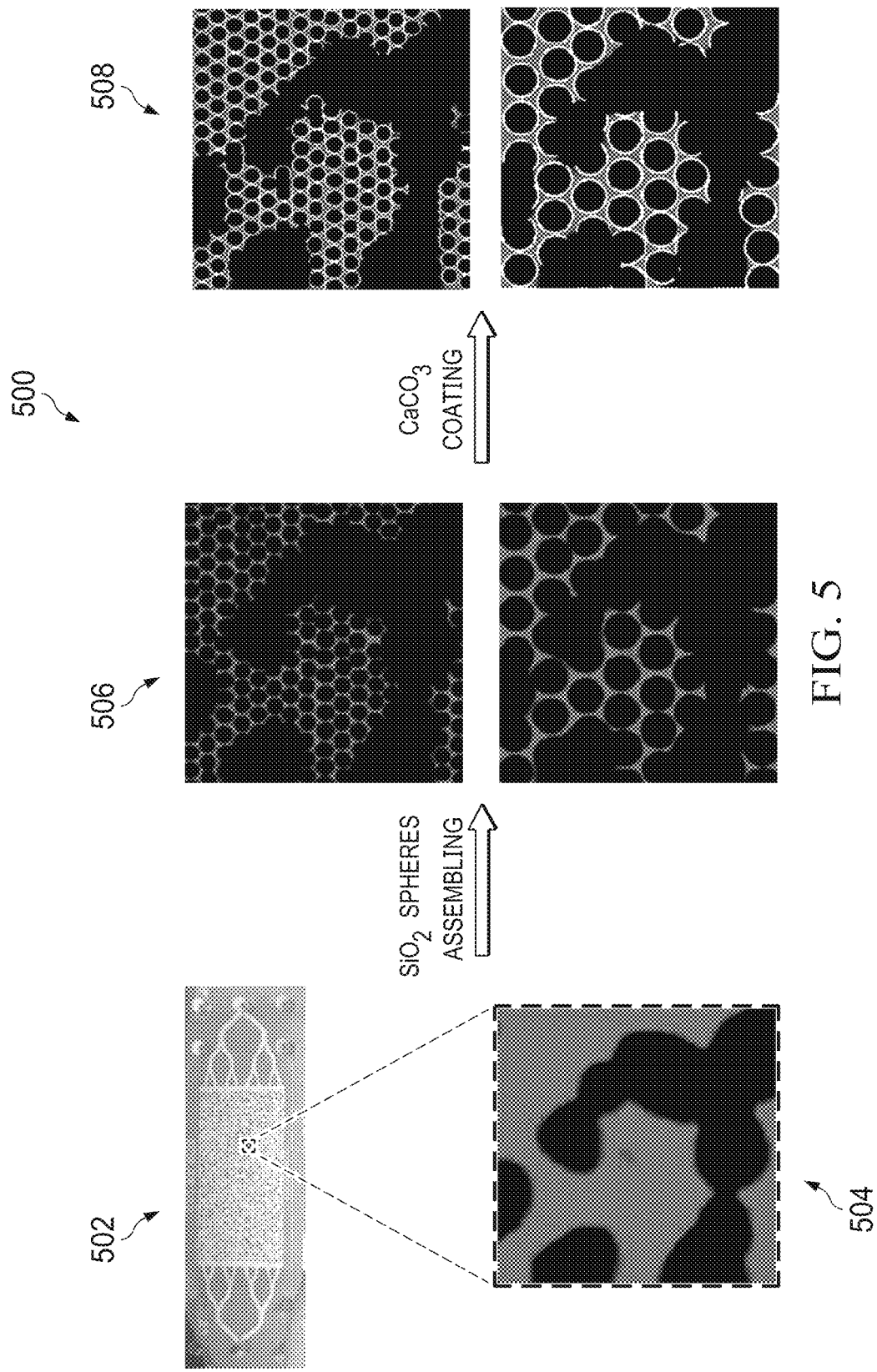
FIG. 5 is a schematic drawing of the method of the assembling of $SiO_2$ spheres in a microfluidic chip, followed by the growth of a calcium carbonate coating, to form a nanofluidic chip.

FIG. 5 is a schematic drawing of the method 500 of the assembling of $SiO_2$ spheres in a microfluidic chip, followed by the growth of a calcium carbonate coating, to form a nanofluidic chip. As shown in FIG. 5, the microfluidic chip 502 is treated to form the surface functionality as described with respect to FIG. 4. The treated microfluidic chip 504 is then injected with the $SiO_2$ spheres to form the precursor nanofluidic chip 506, which is shown at two levels of magnification.

To assemble the spheres into the microfluidic chip, the spheres were suspended in ethanol at a concentration of about 5 to about 10 vol. % and injected to fill the microfluidic channels. During the injection, a filtration paper was used to retain the $SiO_2$ sphere at another end of the chip. When the $SiO_2$ spheres are filled in full for all channels, the chip was vertically placed and let the $SiO_2$ sphere settle and dry naturally in 24 hours. Then the process was repeated to fill additional voids or cracks and dry again.

The precursor nanofluidic chip 506 is then iteratively treated with the calcium chloride and sodium carbonate solutions to form a calcite coating, resulting in the nanofluidic chip 508. The formation of the calcite coating is described further with respect to FIG. 6.

Figure 6:
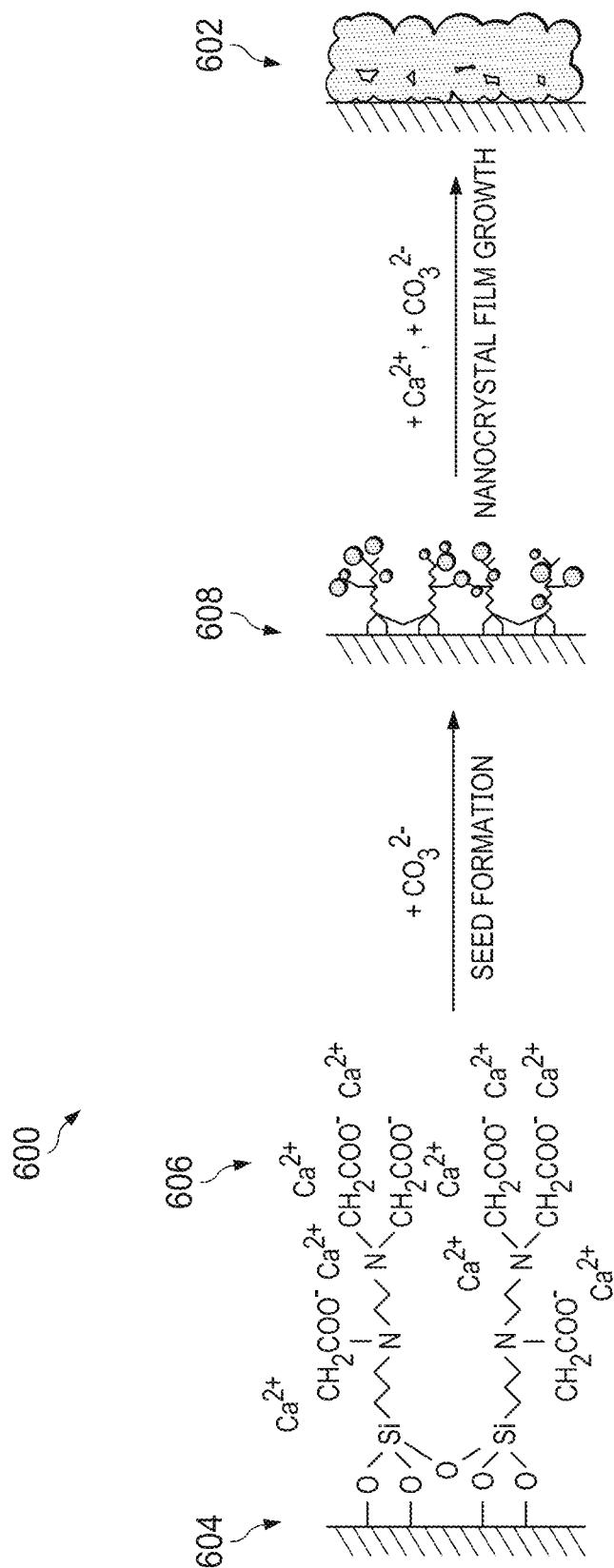
FIG. 6 is a schematic diagram of a method for the growth of a calcium carbonate coating on a functionalized surface.

FIG. 6 is a schematic diagram of a method 600 for the growth of a calcium carbonate coating 602 on a functionalized surface 604. As described herein, the calcium carbonate coating 602 may be grown on the functionalized surfaces of the spheres and the microfluidic chip of the precursor nanofluidic chip 506 (FIG. 5).

For growing the nanocrystals of $CaCO_3$, a 0.05 M solution of $CaCl_2$) in DI water was pumped through the nanochannels of the precursor nanofluidic chip at 0.1 mL/min for 2 min., and allowed to remain in the chip for 10 min., before being removed by a flow of air. Subsequently, a 0.05 M $Na_2CO_3$ solution in DI water was pumped through the channels at 0.1 mL/min for 2 min., and allowed to remain in the chip for 10 min., before being removed by a flow of air. The above process was repeated alternatively for about 5 to 20 times depending on different thickness of $CaCO_3$ layer, and finally rinsed by ethanol and dried at 80° C. in air. Between each injection of a different solution, the precursor nanofluidic chip 506 is rinsed with a flow of 0.05 ml of deionized water to prevent precipitation of calcium carbonate in the channels. Depending on concentrations of $Ca^{2+}$ and $CO_3^{2-}$ used in the coating and the repeated times of the coating process, the thickness of formed $CaCO_3$ nanocrystal layers can be controlled in range of 5-100 nm.

The solutions to form the calcite layer were prepared by dissolving 1.11 g of calcium chloride ($CaCl_2$)) is in 100 ml of deionized water and dissolving 1.06 g of sodium carbonate ($Na_2CO_3$) in 100 ml of deionized water. The sodium ions initially on the carboxylate functionalities, as shown for the functionalized surface 406 (FIG. 4), are replaced with calcium ions by flowing 0.05 ml of the calcium chloride solution through the precursor nanofluidic chip 506 (FIG. 5), forming a calcium substituted surface 606. An initial layer 608 of calcium carbonate, or seed formation, is performed by flowing 0.05 ml of the sodium carbonate solution through the precursor nanofluidic chip 506.

Once the seed formation is completed, forming the initial layer 608, the calcite coating 602 is formed by alternating the flow of 0.05 ml of the calcium chloride solution with a flow of 0.05 ml of the sodium carbonate solution. Between each injection of a different solution, the nanofluidic chip is blown with a flow of air to get rid of access liquid preventing precipitation of calcium carbonate in the channels, and then rinsed with 0.05 ml of DI water. Generally, this is repeated for 5 to 20 cycles.

To test the coating procedure, spheres were coated with calcite as described in the procedure above. These were then imaged using SEM and EDX to confirm the uniform coating of the $SiO_2$ surface with calcium carbonate.

Figure 7A:
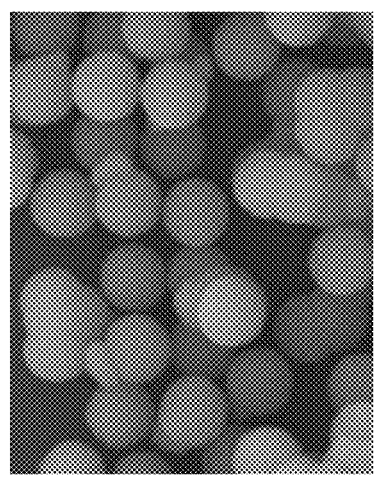
FIGS. 7A-7F are SEM images and EDX showing the elemental mapping of the calcium carbonate coated $SiO_2$ spheres
Figure 7B:
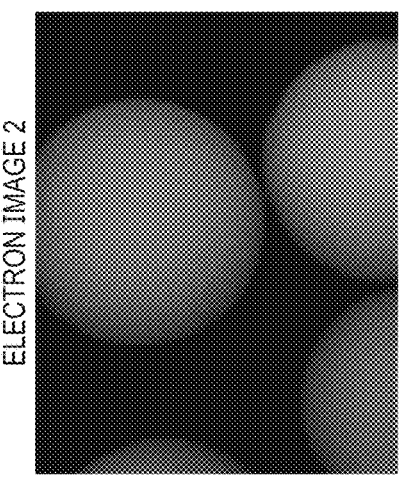

FIGS. 7A-7F are SEM images and EDX showing the elemental mapping of the calcium carbonate coated $SiO_2$ spheres. In FIG. 7A, spheres after coating with calcite are shown. In this example, the spheres are about 650 nm in diameter. A closer view is shown in FIG. 7B.

Figure 7C:
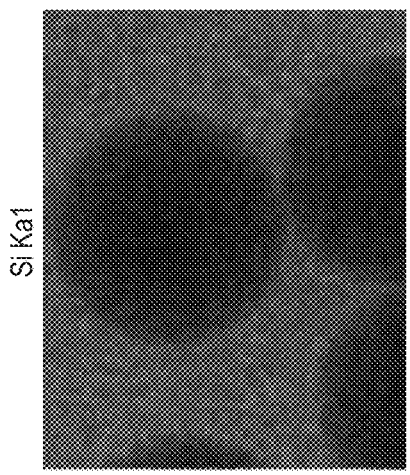
Figure 7D:
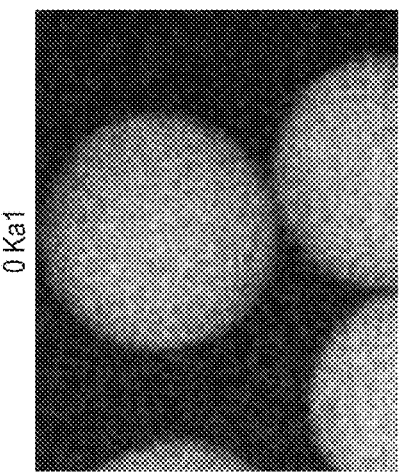

As can be seen in FIG. 7C, a silicon analysis shows that the spheres are dark against the background of silicon wafer, indicating that the $SiO_2$ surface is covered by the surface coating. In FIG. 7D, the oxygen in the calcite layer is clearly shown by the brightness of the spheres against the background.

Figure 7E:
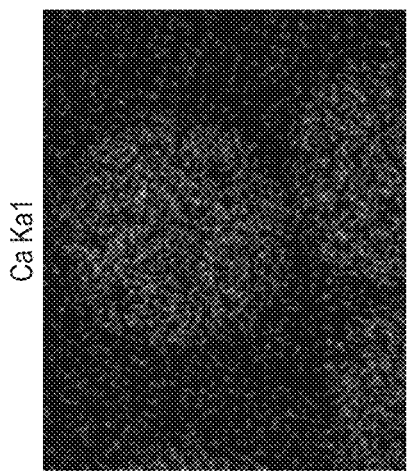
Figure 7F:
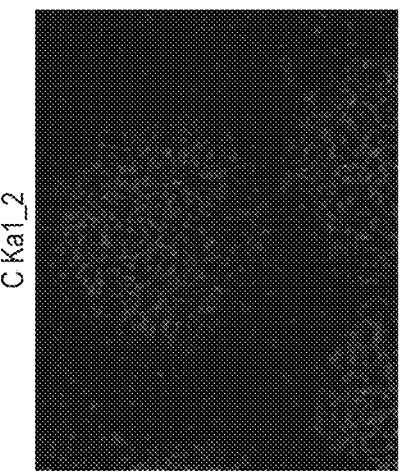

In FIG. 7E, the calcium and the calcite layer is shown by the contrast of the spheres with the background, where the spheres are brighter than the background. In FIG. 7F, the carbon in the calcite layer is shown by the contrast of the spheres with the background, where the spheres are brighter than the background.

An embodiment disclosed herein provides a method for modeling a reservoir with a nanofluidic chip. The method includes fabricating the nanofluidic chip by synthesizing silicon dioxide spheres and functionalizing a surface of the silicon dioxide spheres to form functionalized spheres. A surface of microchannels in a microfluidic chip is functionalized to form a functionalized microfluidic chip. The functionalized spheres are assembled in microchannels of the functionalized microfluidic chip to form a precursor nanofluidic chip. Calcium carbonate nanocrystals are formed on functionalized surfaces of the precursor nanofluidic chip to form the nanofluidic chip.

In an aspect, the silicon dioxide spheres are synthesized to be about 50 to about 2500 nm in diameter. In an aspect, substantially monodisperse silicon dioxide spheres are synthesized. In an aspect, the silicone dioxide spheres are synthesized by hydrolyzing a tetraalkylorthosilicate compound in a water-alcohol mixture with ammonia as a catalyst.

In an aspect, the surface of the silicon dioxide spheres is functionalized by hydrolyzing the surface of the silicon dioxide spheres to form hydroxyl groups. A silane coupling agent comprising carboxylate groups is reacted with the hydrolyze surface through the silane, leaving the carboxylate groups exposed. In an aspect, the surface of the microchannels in a microfluidic chip is functionalized by injecting a reagent to hydrolyze the surface of the microchannels to form hydroxyl groups and injecting a silane coupling agent comprising carboxylate groups, wherein the silane reacts with the hydrolyze surface and the carboxylate groups are exposed.

In an aspect, the functionalized spheres are assailed channels of the functionalized microfluidic chip by suspending the functional spheres and ethanol to form a colloidal suspension. The colloidal suspension is injected into the microfluidic chip, wherein the functionalized spheres are trapped in the microchannels of the microfluidic chip to assemble into random close-packed structures.

In an aspect, the calcium carbonate nanocrystals are formed by flowing a calcium chloride solution through the precursor nanofluidic chip and iterating between flowing a sodium carbonate solution through the precursor nanofluidic chip and flowing the calcium chloride solution through the precursor nanofluidic chip. In an aspect, the iteration is performed for between five and 20 cycles forming a layer of calcium carbonate nanocrystals having a thickness of about 5 nm to about 100 nm. In an aspect, and magnesium chloride solution, or a mixed calcium chloride and magnesium chloride solution, is flowed through the precursor nanofluidic during and iteration.

In an aspect, a size of channels in the nanofluidic chip is controlled by selecting a size of the silicon dioxide spheres, wherein the size of channels in a network of voids is between about 10 nm to about 1000 nm. In an aspect, the precursor nanofluidic chip is assembled from functionalized spheres of two different sizes and generating mixed nanoscale porosity.

In an aspect, the nanofluidic chip is used to study oil-water phase behavior in nanoscale pores of the reservoir. In an aspect, the nanofluidic chip is used to study rock-fluid interactions in nanoscale pores of the reservoir. In an aspect, the nanofluidic chip is used in microscopic studies of interactions between fluids and surfaces. In an aspect, an optically transparent nanofluidic chip is used in spectroscopic studies of interactions between fluids and surfaces.

Another embodiment described herein provides a nanofluidic chip for reservoir modeling includes a microfluidic chip comprising microchannels etched in a substrate. Silica spheres assembled in the microchannels form nanochannels. A carbonate coating is disposed over the surfaces of the nanochannels and the silica spheres.

In an aspect, the nanofluidic chip includes nanochannels of less than 1000 nm. In an aspect, the nanofluidic chip includes nanochannels of less than 20 nm.

In an aspect, the carbonate coating includes calcium. In an aspect, the carbonate coating includes magnesium. In an aspect, the carbonate coating includes both calcium and magnesium. In an aspect, the carbonate coating includes aluminum, zinc, iron, calcium, magnesium, titanium, or vanadium, or any combinations thereof.

Other implementations are also within the scope of the following claims.

What is claimed is:

1. A method for modeling a reservoir with a nanofluidic chip, comprising fabricating the nanofluidic chip by:
    synthesizing silicon dioxide spheres;
    functionalizing a surface of the silicon dioxide spheres to form functionalized spheres;
    functionalizing a surface of microchannels in a microfluidic chip to form a functionalized microfluidic chip;
    assembling the functionalized spheres in microchannels of the functionalized microfluidic chip to form a precursor nanofluidic chip; and
    forming calcium carbonate nanocrystals on functionalized surfaces of the precursor nanofluidic chip to form the nanofluidic chip.

2. The method of claim 1, further comprising synthesizing silicon dioxide spheres of about 50 to about 2500 nm in diameter.

3. The method of claim 1, further comprising synthesizing substantially monodisperse silicon dioxide spheres.

4. The method of claim 3, further comprising synthesizing the silicon dioxide spheres by hydrolyzing a tetraalkylorthosilicate compound in a water-alcohol mixture with ammonia as a catalyst.

5. The method of claim 1, further comprising functionalizing the surface of the silicon dioxide spheres by:
    hydrolyzing the surface of the silicon dioxide spheres to form hydroxyl groups; and
    injecting a silane coupling agent comprising carboxylate groups, wherein the silane reacts with the hydrolyzed surface and the carboxylate groups are exposed.

6. The method of claim 1, further comprising functionalizing the surface of the microchannels in the microfluidic chip by:
    injecting a reagent to hydrolyze the surface of the microchannels to form hydroxyl groups; and
    injecting a silane coupling agent comprising carboxylate groups, wherein the silane reacts with the hydrolyzed surface and the carboxylate groups are exposed.

7. The method of claim 1, further comprising assembling the functionalized spheres in the microchannels of the functionalized microfluidic chip by:
    suspending the functionalized spheres in ethanol to form a colloidal suspension; and
    injecting the colloidal suspension into the microfluidic chip, wherein the functionalized spheres are trapped in the microchannels of the microfluidic chip to assemble into random close-packed structures.

8. The method of claim 1, further comprising forming the calcium carbonate nanocrystals by:
    flowing a calcium chloride solution through the precursor nanofluidic chip; and
    iterating between:
        flowing a sodium carbonate solution through the precursor nanofluidic chip; and
        flowing the calcium chloride solution through the precursor nanofluidic chip.

9. The method of claim 8, comprising:
    iterating for between five and 20 cycles; and
    forming a layer of calcium carbonate nanocrystals having a thickness of about 5 nm to about 100 nm.

10. The method of claim 8, further comprising flowing a magnesium chloride solution, or a mixed calcium chloride and magnesium chloride solution, through the precursor nanofluidic chip during an iteration.

11. The method of claim 1, further comprising controlling a size of channels in the nanofluidic chip by selecting a size of the silicon dioxide spheres, wherein the size of channels in a network of voids is between about 10 nm to about 1000 nm.

12. The method of claim 1, further comprising:
    assembling the precursor nanofluidic chip from functionalized spheres of two different sizes; and
    generating mixed nanoscale porosity.

13. The method of claim 1, further comprising using the nanofluidic chip to study oil-water phase behavior in nanoscale pores of the reservoir.

14. The method of claim 1, further comprising using the nanofluidic chip to study rock-fluid interactions in nanoscale pores of the reservoir.

15. The method of claim 1, further comprising using an optically transparent nanofluidic chip in microscopic studies of interactions between fluids and surfaces.

16. The method of claim 1, further comprising using the nanofluidic chip in spectroscopic studies of interactions between fluids and surfaces.

* * * * *